US011850235B2

(12) United States Patent
Staedtke et al.

(10) Patent No.: US 11,850,235 B2
(45) Date of Patent: Dec. 26, 2023

(54) PREVENTATIVE EFFECT OF MEBENDAZOLE AGAINST MALIGNANCIES IN NEUROFIBROMATOSIS

(71) Applicant: THE JOHNS HOPKINS UNIVERSITY, Baltimore, MD (US)

(72) Inventors: Verena Staedtke, Baltimore, MD (US); Renyuan Bai, Baltimore, MD (US)

(73) Assignee: The Johns Hopkins University, Baltimore, MD (US)

(*) Notice: Subject to any disclaimer, the term of this patent is extended or adjusted under 35 U.S.C. 154(b) by 76 days.

(21) Appl. No.: 17/369,763

(22) Filed: Jul. 7, 2021

(65) Prior Publication Data

US 2023/0035885 A1 Feb. 2, 2023

(51) Int. Cl.
*A61K 31/4184* (2006.01)
*A61K 31/635* (2006.01)
*A61P 35/00* (2006.01)

(52) U.S. Cl.
CPC ........ *A61K 31/4184* (2013.01); *A61K 31/635* (2013.01); *A61P 35/00* (2018.01)

(58) Field of Classification Search
CPC .... A61P 35/00; A61K 31/635; A61K 31/4184
See application file for complete search history.

(56) References Cited

PUBLICATIONS

Staedtke, et al., Preventative Effect of Mebendazole against Malignancies in Neurofibromatosis 1, Genes 11(7), 762 (2020) (Year: 2020).*

* cited by examiner

*Primary Examiner* — Erich A Leeser
(74) *Attorney, Agent, or Firm* — DLA Piper LLP (US)

(57) ABSTRACT

The invention provides methods of delaying or preventing NF1-related malignancies or tumors using mebendazole. The administration of mebendazole results in decreased Ras activation in NF1-related tumor cells. Invention methods include the use of a cyclooxygenase-2 inhibitor such as celecoxib in combination with mebendazole. The methods include methods of treatment and methods of prevention or delaying of neurofibromatosis type 1-related malignancies or tumors.

20 Claims, 9 Drawing Sheets

Specification includes a Sequence Listing.

PREVENTATIVE EFFECT OF MEBENDAZOLE AGAINST MALIGNANCIES IN NEUROFIBROMATOSIS

INCORPORATION OF SEQUENCE LISTING

The material in the accompanying sequence listing is hereby incorporated by reference into this application. The accompanying sequence listing text file, name JHU4380_(331323-001395)_SL.txt, was created on Jul. 1, 2021, and is 3 kb. The file can be assessed using Microsoft Word on a computer that uses Windows OS.

BACKGROUND OF THE INVENTION

Field of the Invention

The present invention relates generally to methods for preventing or delaying the development of neurofibromatosis type 1-related malignancies, and more specifically to the use of mebendazole, alone or in combination with a cyclooxygenase-2 inhibitor, for the prevention of neurofibromatosis type 1-related malignancies.

Background Information

RASopathyNeurofibromatosis type 1 (NF1) is an autosomal dominant hereditary cancer predisposition syndrome that affects ~1:3000 individuals. It is caused by mutations in the neurofibromin 1 (Nf1) tumor suppressor gene, which encodes the GTPase-activating protein-related domain (GRD) that catalyzes the inactivation of Ras by accelerating guanosine triphosphate (GTP) hydrolysis to guanosine diphosphate (GDP). In NF1 individuals, loss of Nf1 results in high levels of activated Ras, leading to the formation of multiple benign and malignant tumors via multiple effector pathways, including the Ras-MAPK pathway, with subsequent activation of the RAF-MEK-ERK cascade.

Patients with NF1 have an increased cancer risk and mortality, and lower survival compared with the general population. Based on the Finnish NF1 Registry, the estimated lifetime cancer risk in patients with NF1 is 59.6%, with an estimated cumulative cancer risk of ~25% and ~39% by age 30 and 50 years, whereas the respective percentages in the general Finnish population are much lower, at 30.8%, 0.8% and 3.9%. The most common NF1-related malignancies are of nervous system origin, such as malignant peripheral nerve sheath tumors (MPNSTs) and astrocytomas, which comprise 63% of all malignancies. Other malignancies include breast cancer, rhabdomyosarcomas, pheochromocytoma, gastrointestinal stromal tumor (GIST), malignant fibrous histiocytoma, and thyroid cancer.

NF1-related malignancies, including MPNSTs, typically manifest early in life and are responsible for the relative excess in cancer incidence and mortality observed in children and young adults afflicted with NF1. Those malignancies are typically very difficult to treat and current therapies have shown little long-term benefit despite extensive research efforts; however, early chemoprevention to delay cancer occurrence and reduce cancer risk remains largely unexplored.

SUMMARY OF THE INVENTION

The present invention is based on the seminal discovery that mebendazole, alone or in combination with a cyclooxygenase-2 inhibitor, can be used for preventing or delaying the development of neurofibromatosis type 1-related malignancies. Additionally, mebendazole, alone or in combination with a cyclooxygenase-2 inhibitor, can be used for reducing the risk for developing neurofibromatosis type 1-related malignancies.

In one embodiment, the present invention provides a method of preventing or delaying the development of a neurofibromatosis type 1 (NF1)-related malignancy or cancer in a subject having NF1 including administering to the subject a therapeutically effective amount of mebendazole (MBZ), thereby preventing or delaying the development of the NF1-related malignancy or cancer.

In one aspect, the NF1-related malignancy or cancer is selected from the group consisting of malignant peripheral nerve sheath tumor (MPNST), astrocytoma, breast cancer, rhabdomyosarcoma, pheochromocytoma, gastrointestinal stromal tumor (GIST), malignant fibrous histiocytoma and thyroid cancer. In many aspects, the NF1-related cancer is MPNST. In another aspect, MBZ inhibits or reduces NF1-related cancer cell growth. In one aspect, inhibiting or reducing NF1-related cancer cell growth includes reducing Ras activation, reducing GTP-bound Ras levels and/or reducing phospho-ERK (pERK) levels in NF1-related cancer cells. In another aspect, administering MBZ increases survival of the subject. In one aspect, the therapeutically effective amount of MBZ includes about 25-50 mg/kg MBZ. In another aspect, the method further includes administering to the subject a therapeutically effective amount of a cyclooxygenase-2 (COX-2) inhibitor. In some aspects, the COX-2 inhibitor is celecoxib (CXB). In one aspect, the therapeutically effective amount of CXB includes about 100-200 mg/day CXB.

In another embodiment, the invention provides a method of reducing a risk of developing a neurofibromatosis type 1 (NF1)-related malignancy or cancer in a subject having NF1 including administering to the subject a therapeutically effective amount of mebendazole (MBZ), thereby reducing the risk of developing a NF1-related malignancy or cancer.

In one aspect, the NF1-related cancer is MPNST. In another aspect, MBZ inhibits or reduces NF1-related cancer cell growth. In one aspect, inhibiting or reducing NF1-related cancer cell growth includes reducing Ras activation, reducing GTP-bound Ras levels and/or reducing phospho-ERK (pERK) levels in NF1-related cancer cells. In one aspect, the method further includes administering to the subject a therapeutically effective amount of a cyclooxygenase-2 (COX-2) inhibitor. In some aspects, the COX-2 inhibitor is celecoxib (CXB).

In an additional embodiment, the invention provides a pharmaceutical composition including a therapeutically effective amount of mebendazole (MBZ), a therapeutically effective amount of a cyclooxygenase-2 (COX-2) inhibitor and a pharmaceutically acceptable carrier.

In one aspect, the COX-2 inhibitor is celecoxib (CXB).

In a further embodiment, the invention provides a method of reducing the risk of developing a neurofibromatosis type 1 (NF1)-related malignancy or cancer in a subject having NF1 including administering to the subject a composition including a therapeutically effective amount of mebendazole (MBZ), a therapeutically effective amount of a cyclooxygenase-2 (COX-2) inhibitor and a pharmaceutically acceptable carrier, thereby reducing the risk of developing a NF1-related malignancy or cancer.

In yet another embodiment, the invention provides a method of preventing or delaying the development of a neurofibromatosis type 1 (NF1)-related malignancy or cancer in a subject having NF1 including administering to the subject a composition including a therapeutically effective amount of mebendazole (MBZ), a therapeutically effective amount of a cyclooxygenase-2 (COX-2) inhibitor and a pharmaceutically acceptable carrier, thereby preventing or delaying the development of the NF1-related malignancy or cancer.

BRIEF DESCRIPTION OF THE DRAWINGS

FIG. 1A is a graph showing the IC50 of MBZ administered to NF90-8 and sNF96.2 cells. FIG. 1B shows an immunoblot of activated GTP-bound Ras.

FIG. 2A is a graph showing the 30-day weight of male mice on MBZ diet. FIG. 2B is a graph showing the 30-day weight of female mice on MBZ diet.

FIG. 3A is a Kaplan-Meier curve showing the overall survival in male and female mice. FIG. 3B is a Kaplan-Meier curve showing the overall survival in male mice. FIG. 3C is a Kaplan-Meier curve showing the overall survival in female mice. FIG. 3D is a Kaplan-Meier curve showing the solid malignancy-related mortality in male and female mice. FIG. 3E is a Kaplan-Meier curve showing the solid malignancy-related mortality in male mice. FIG. 3F is a Kaplan-Meier curve showing the solid malignancy-related mortality in female mice. FIG. 3G is a Kaplan-Meier curve showing the non-solid malignancy-related and unknown mortality in male and female mice. FIG. 3H is a Kaplan-Meier curve showing the non-solid malignancy-related and unknown mortality in male mice. FIG. 3I is a Kaplan-Meier curve showing the non-solid malignancy-related and unknown mortality in female mice. FIG. 3J is a graph bar showing the percentage distribution of malignancy-related deaths of MBZ-treated NPcis mice compared to control in male and female mice. FIG. 3K is a graph bar showing the percentage distribution of malignancy-related deaths of MBZ-treated NPcis mice compared to control in male mice. FIG. 3L is a graph bar showing the percentage distribution of malignancy-related deaths of MBZ-treated NPcis mice compared to control in female mine.

FIG. 5A is a Kaplan-Meier curve showing the overall survival in male and female mice. FIG. 5B is a Kaplan-Meier curve showing the overall survival in male mice. FIG. 5C is a Kaplan-Meier curve showing the overall survival in female mice. FIG. 5D is a Kaplan-Meier curve showing the solid malignancy-related mortality in male and female mice. FIG. 5E is a Kaplan-Meier curve showing the solid malignancy-related mortality in male mice. FIG. 5F is a Kaplan-Meier curve showing the solid malignancy-related mortality in female mice. FIG. 5G is a Kaplan-Meier curve showing the non-solid malignancy-related and unknown mortality in male and female mice. FIG. 5H is a Kaplan-Meier curve showing the non-solid malignancy-related and unknown mortality in male mice. FIG. 5I is a Kaplan-Meier curve showing the non-solid malignancy-related and unknown mortality in female mice. FIG. 5J is a graph bar showing the percentage distribution of malignancy-related deaths of SUL- and CXB-treated NPcis mice compared to control in male and female mice. FIG. 5K is a graph bar showing the percentage distribution of malignancy-related deaths of SUL- and CXB-treated NPcis mice compared to control in male mice. FIG. 5L is a graph bar showing the percentage distribution of malignancy-related deaths of SUL- and CXB-treated NPcis mice compared to control in female mice.

FIG. 6A is a Kaplan-Meier curve showing the overall survival in male and female mice. FIG. 6B is a Kaplan-Meier curve showing the overall survival in male mice. FIG. 6C is a Kaplan-Meier curve showing the overall survival in female mice. FIG. 6D is a Kaplan-Meier curve showing the solid malignancy-related mortality in male and female mice. FIG. 6E is a Kaplan-Meier curve showing the solid malignancy-related mortality in male mice. FIG. 6F is a Kaplan-Meier curve showing the solid malignancy-related mortality in female mice. FIG. 6G is a Kaplan-Meier curve showing the non-solid malignancy-related and unknown mortality in male and female mice. FIG. 6H is a Kaplan-Meier curve showing the non-solid malignancy-related and unknown mortality in male mice. FIG. 6I is a Kaplan-Meier curve showing the non-solid malignancy-related and unknown mortality in female mice. FIG. 6J is a graph bar showing the percentage distribution of malignancy-related deaths of MBZ−, CXB− and MBZ+CXB-treated NPcis mice compared to control in male and female mice. FIG. 6K is a graph bar showing the percentage distribution of malignancy-related deaths of MBZ−, CXB− and MBZ+CXB-treated NPcis mice compared to control in male mice. FIG. 6L is a graph bar showing the percentage distribution of malignancy-related deaths of MBZ−, CXB− and MBZ+CXB-treated NPcis mice compared to control in female mice.

DETAILED DESCRIPTION OF THE INVENTION

Figure 1A:
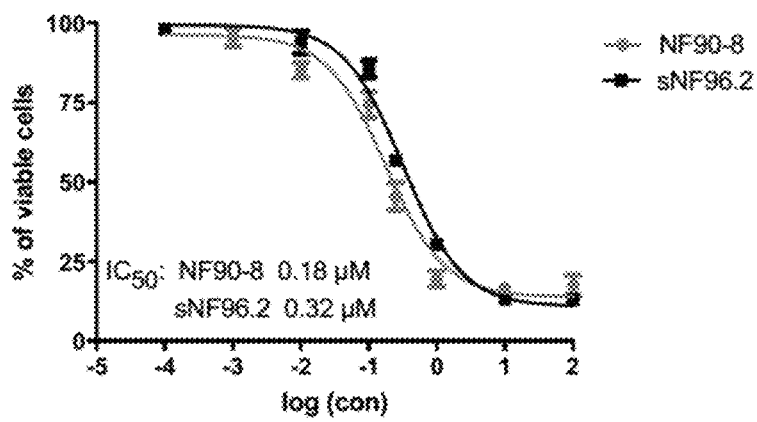
FIGS. 1A-1B illustrate the effect of mebendazole (MBZ) on malignant peripheral nerve sheath tumor (MPNST) cells and Ras activity.

The present invention is based on the seminal discovery that mebendazole, alone or in combination with cyclooxygenase-2 inhibitor, can be used for preventing or delaying the development of neurofibromatosis type 1-related malignancies. Additionally, mebendazole, alone or in combination with a cyclooxygenase-2 inhibitor, can be used for reducing the risk for developing neurofibromatosis type 1-related malignancies.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

All publications, patents, and patent applications mentioned in this specification are herein incorporated by reference to the same extent as if each individual publication, patent, or patent application was specifically and individually indicated to be incorporated by reference.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, it will be understood that modifications and variations are encompassed within the spirit and scope of the instant disclosure. The preferred methods and materials are now described.

One of the most common NF1-related malignancies is malignant peripheral nerve sheath tumors (MPNSTs). MPNST is a very aggressive spindle cell sarcoma which accounts for the majority of cancer deaths in all NF1 patients and is a hallmark complication of this condition. MPNST may arise from any of the pre-existing plexiform neurofibromas distributed throughout a patient's body. Unfortunately, there is no way of knowing which individual and, more specifically, which lesions within any one individual are likely to behave in a malignant fashion and thus many patients require regular screening with standard radiographic techniques such as MRI and PET/CT. Patients with Nf1 microdeletion, i.e., a large deletion of the Nf1 gene and its flanking regions, are especially susceptible to MPNSTs.

The development of new pharmaceutical agents for chemoprevention is a long and difficult process. One strategy is to discover new uses for compounds with an established track record of safe and long-term use in humans, such as mebendazole, alone or in combination with already known cancer prevention agents. Examples of such agents include cyclooxygenase-2 (COX-2) inhibitors.

Mebendazole (MBZ), an FDA-approved low molecular weight benzimidazole derivative with a lengthy track record of safe long-term human use, was identified as efficient at significantly reducing tumor growth and improving survival in the animal models of glioblastoma multiforme (GBM) and medulloblastoma (Sonic Hedgehog (SHH) Group and c-Myc/OTX2 amplified Group 3) and also reducing tumor formation in a Familial Adenomatous Polyposis (FAP) colon cancer model. A number of mechanisms for MBZ's antineoplastic activity have been proposed, including microtubule disruption, pro-apoptosis, and the inhibition of growth factor signaling through the blockage of various tyrosine kinases, particularly VEGFR2.

The effects of COX-2 inhibitors are mediated through the inhibition of angiogenesis via decreasing COX-2-induced vascular endothelial growth factor (VEGF) production and apoptosis via altered caspase signaling. Notably, COX-2 overexpression has been found in a variety of sarcomas and has been associated with poor prognosis, thus suggesting that COX-2 inhibitors could play a role in NF1 cancer prevention.

In one embodiment, the present invention provides a method of preventing or delaying the development of a neurofibromatosis type 1 (NF1)-related malignancy or cancer in a subject having NF1 including administering to the subject a therapeutically effective amount of mebendazole (MBZ), thereby preventing or delaying the development of the NF1-related malignancy or cancer.

As used herein, "neoplasm", "tumor", "cancer" and "malignancy" including grammatical variations thereof, can be used interchangeably and refer to new and abnormal growth of tissue, which may be benign or cancerous. In a related aspect, the neoplasm is indicative of a neoplastic disease or disorder, including but not limited to, various cancers. For example, such cancers can include prostate, pancreatic, biliary, colon, rectal, liver, kidney, lung, testicular, breast, ovarian, pancreatic, brain, and head and neck cancers, melanoma, sarcoma, multiple myeloma, leukemia, lymphoma, and the like. The terms "malignancy" and "cancer" refer to a group diseases characterized by abnormal and uncontrolled cell proliferation starting at one site (primary site) with the potential to invade and to spread to others sites (secondary sites, metastases) which differentiate cancer (malignant tumor) from benign tumor. Virtually all the organs can be affected, leading to more than 100 types of cancer that can affect humans. Cancers can result from many causes including genetic predisposition, viral infection, exposure to ionizing radiation, exposure environmental pollutant, tobacco and or alcohol use, obesity, poor diet, lack of physical activity or any combination thereof.

The methods described herein relate to NF1-related malignancy or cancer.

Neurofibromatosis type 1 (NF1) is a complex multisystem human disorder caused by the mutation of a gene on chromosome 17 that is responsible for production of neurofibromin, which is needed for normal function in many human cell types. NF1 causes tumors along the nervous system which can grow anywhere on the body. NF1 is an autosomal dominant disorder, which means that mutation or deletion of one copy (or allele) of the Nf1 gene is sufficient for the development of NF1, although presentation varies widely and is often different even between relatives affected by NF1. Common symptoms of NF1 include brownish-red spots in the colored part of the eye called Lisch nodules, benign skin tumors called neurofibromas, and larger benign tumors of nerves called plexiform neurofibromas, scoliosis (curvature of the spine), learning disabilities, vision disorders, mental disabilities, multiple café au lait spots and epilepsy. NF1 affected individuals also have a much higher rate of cancer and cardiovascular disease than the population in general.

NF1 is a developmental syndrome caused by germline mutations in neurofibromin, a gene that is involved in the RAS pathway (RASopathy). Due to its rarity and to the fact that genetic diagnosis has been used only in recent years, in the past NF1 was in some cases confused with Legius syndrome, another syndrome with vaguely similar symptoms, including cafe-au-lait spots.

As used herein, the terms "NF1-related malignancy" or "NF1-related cancer" refer to the tumors that are associated with Nf1 mutations. Most tumors associated with NF1 are benign (non-cancerous) skin tumors, which grow on nerves throughout the body. Neurofibromas (NFs) are the most common type of tumor in people with NF1. The two major types of neurofibromas are dermal (sub-cutaneous) neurofibromas, and plexiform neurofibromas. Dermal neurofibromas are small, nodule-like tumors that grow on or just under the surface of the skin. They can be painful, itchy, disfiguring or tender when touched, but they have no known potential to become cancerous. Dermal neurofibromas may also be asymptomatic. Plexiform neurofibromas are larger tumors that develop inside the body and tend to wrap in and around nerves, blood vessels and other structures in the body. They can be deep inside the body or closer to the skin. Plexiform neurofibromas can cause pain, numbness, weakness, and disfigurement. These tumors do have a small chance of becoming a cancer. Plexiform neurofibromas may also be asymptomatic. Cancerous tumors associated with NF1 also include gliomas, a type of brain tumor that originates in the glial cells in the brain, and malignant peripheral nerve sheath tumors (MPNSTs). These are cancerous tumors that grow on the nerve sheath, the cells surrounding the nerve.

In one aspect, the NF1-related malignancy or cancer is selected from the group consisting of malignant peripheral nerve sheath tumor (MPNST), astrocytoma, breast cancer, rhabdomyosarcoma, pheochromocytoma, gastrointestinal stromal tumor (GIST), malignant fibrous histiocytoma and thyroid cancer.

In many aspects, the NF1-related cancer is MPNST.

The methods described herein relate to preventing or delaying the development of NF1-related malignancy or cancer.

By "preventing" the development of NF1-related malignancy or cancer, it is meant that the method is used before the health effects occur (primary prevention), at the earliest stage of the disease (secondary prevention, usually after screening of at-risk patients to identify lesions early), or after the diagnosis of the malignancy, as part of the management of the malignancy (to slow down or stop its development, tertiary prevention). By "delaying" the development of NF1-related malignancy or cancer, it is meant that the method extends the time by which a subject develops a NF1-related malignancy or cancer (as compared to the time by which the subject would have developed the NF1-related malignancy or cancer in the absence of the administration of MBZ). For example, the delay may be days, months or years as compared with an NF1 subject not treated with MBZ would develop cancer.

The methods described herein relate to the administration of a therapeutically effective amount of mebendazole (MBZ) to the subject.

The term "subject" as used herein refers to any individual or patient to which the subject methods are performed. Generally, the subject is human, although as will be appreciated by those in the art, the subject may be an animal. Thus other animals, including vertebrate such as rodents (including mice, rats, hamsters and guinea pigs), cats, dogs, rabbits, farm animals including cows, horses, goats, sheep, pigs, chickens, etc., and primates (including monkeys, chimpanzees, orangutans and gorillas) are included within the definition of subject. The subject in the methods described herein has NF1. By "having NF1" or "having a NF1 disease" it is meant that the subject has been diagnosed with a mutation in the Nf1 gene and/or that the subject has been diagnosed with an NF1 disease based on the symptoms of the subject, which would be known to those of skill in the art.

The terms "therapeutically effective amount", "effective dose," "therapeutically effective dose", "effective amount," or the like refer to that amount of the subject compound that will elicit the biological or medical response of a tissue, system, animal or human that is being sought by the researcher, veterinarian, medical doctor or other clinician. Generally, the response is either amelioration of symptoms in a patient or a desired biological outcome (e.g., treatment or prevention of a NF1-related malignancy). Such amount should be sufficient to treat a NF1-related malignancy, or to delay the development of such malignancy. The effective amount can be determined as described herein.

In one aspect, the therapeutically effective amount of MBZ includes about 1-100, 10-100, 10-75, 20-75, or 25-60 mg/kg MBZ. In a particular aspect, the dosage is about 25-50 mg/kg MBZ. By "about 25-50 mg/kg", it is meant that MBZ is to be administered within a dosing range of about 25-50 mg/kg for adults. For example, an effective amount of MBZ includes about 20, about 25, about 30, about 35, about 40, about 45, about 50, or about 55 mg/kg MBZ, for an adult subject (e.g., 18-year-old and older). The dosing range can be adjusted for the treatment of children, following rules and guidelines known in the art.

The terms "administration of" and or "administering" should be understood to mean providing a pharmaceutical composition in a therapeutically effective amount to the subject in need of treatment. Administration routes can be enteral, topical or parenteral. A preferred route of administration is oral. As such, administration routes include but are not limited to intracutaneous, subcutaneous, intravenous, intraperitoneal, intraarterial, intrathecal, intracapsular, intraorbital, intracardiac, intradermal, transdermal, transtracheal, subcuticular, intraarticulare, subcapsular, subarachnoid, intraspinal and intrasternal, oral, sublingual buccal, rectal, vaginal, nasal ocular administrations, as well infusion, inhalation, and nebulization. The phrases "parenteral administration" and "administered parenterally" as used herein means modes of administration other than enteral and topical administration.

Mebendazole is a highly effective, broad-spectrum anti-helminthic indicated for the treatment of nematode infestations, including roundworm, hookworm, whipworm, threadworm, pinworm, and the intestinal form of trichinosis prior to its spread into the tissues beyond the digestive tract. Mebendazole works by selectively inhibiting the synthesis of microtubules via binding to colchicine binding site of β-tubulin, thereby blocking polymerization of tubulin dimers in intestinal cells of parasites. Disruption of cytoplasmic microtubules leads to blocking the uptake of glucose and other nutrients, resulting in the gradual immobilization and eventual death of the helminths. Mebendazole inhibits polymerization of tubulin dimers, thereby disrupting essential microtubule structures such as mitotic spindle. Disassembly of mitotic spindle then leads to apoptosis mediated via dephosphorylation of Bcl-2 which allows pro-apoptotic protein Bax to dimerize and initiate programmed cell death. Several studies have shown that mebendazole exhibits potent antitumor properties. For example, MBZ significantly inhibited cancer cell growth, migration, and metastatic formation of adrenocortical carcinoma, both in vitro and in vivo; treatment of lung cancer cell lines with MBZ caused mitotic arrest, followed by apoptotic cell death with the feature of caspase activation and cytochrome c release; MBZ induced a dose- and time-dependent apoptotic response in human lung cancer cell lines, and apoptosis via Bcl-2 inactivation in chemoresistant melanoma cells.

The present invention is based on the discovery of the efficacy of MBZ to inhibit or reduce the growth of cancer cells presenting an NF1 mutation.

Nf1 is a tumor suppressor gene, which encodes the GTPase-activating protein-related domain (GRD) that catalyzes the inactivation of Ras by accelerating guanosine triphosphate (GTP) hydrolysis to guanosine diphosphate (GDP). In NF1 individuals, loss of Nf1 results in high levels of activated Ras, leading to the formation of multiple benign and malignant tumors via multiple effector pathways, including the Ras-MAPK pathway, with subsequent activation of the RAF-MEK-ERK cascade. As detailed below in the examples, the present invention describes how MBZ inhibits NF1 deficient cells' growth, reduces Ras activation, reduces GTP-bound Ras levels, and reduces reducing phospho-ERK (pERK) levels.

In one aspect MBZ inhibits or reduces NF1-related cancer cell growth.

In some aspects, inhibiting or reducing NF1-related cancer cell growth includes reducing Ras activation in NF1-related cancer cells. In other aspects, inhibiting or reducing NF1-related cancer cell growth includes reducing GTP-bound Ras levels in NF1-related cancer cells. In other aspects, inhibiting or reducing NF1-related cancer cell growth includes reducing pERK levels in NF1-related cancer cells.

The diagnosis of an NF1 disease in a subject is associated with an increased risk of developing NF1-related malignancies or cancers, which are responsible for a reduction of the survival of the subject. By preventing or delaying the development of a NF1-related malignancy or cancer, the method described herein limits or prevents this reduction of the subject survival.

In some aspects, administering MBZ increases survival of the subject by at least 1%, 10%, 20%, 30%, 40%, 50%, 60%, 70%, 80%, 90% or more as compared with a subject not treated with MBZ.

In another aspect, the method further includes administering to the subject a therapeutically effective amount of a cyclooxygenase-2 (COX-2) inhibitor.

In some aspects, administration can be in combination with one or more additional therapeutic agents. The phrases "combination therapy", "combined with" and the like refer to the use of more than one medication or treatment simultaneously to increase the response. The composition of the present invention might for example be used in combination with other drugs or treatment in use to treat NF1-related malignancy. Specifically, the administration of MBZ to a subject can be in combination with the administration of a COX-2 inhibitor. Such therapies can be administered prior to, simultaneously with, or following administration of the composition of the present invention (e.g. prior to, simultaneously with, or following the administration of MBZ). In one aspect, the administration of MBZ is concurrent with the administration of the COX-2 inhibitor.

Cyclooxygenases (COX), officially known as prostaglandin-endoperoxide synthase (PTGS), are enzymes responsible for the formation of prostanoids, including thromboxane and prostaglandins such as prostacyclin, from arachidonic acid. There are two isozymes found in humans, PTGS1 and PTGS2, referred to as COX-1 and COX-2. Pharmaceutical inhibition of COX can provide relief from the symptoms of inflammation and pain. Nonsteroidal anti-inflammatory drugs (NSAIDs), such as aspirin and ibuprofen, exert their effects through inhibition of COX. Those that are specific to the COX-2 isozyme are called COX-2 inhibitors. The active metabolite (AM404) of paracetamol believed to provide most or all of its analgesic effects is a COX inhibitor, and this is believed to provide part of its effect. COX-2 inhibitors are a type of nonsteroidal anti-inflammatory drug (NSAID) that directly targets COX-2. Targeting selectivity for COX-2 reduces the risk of peptic ulceration. COX-2 appears to be related to cancers and abnormal growths in the intestinal tract. COX inhibitors have been shown to reduce the occurrence of cancers and pre-cancerous growths. Celebrex has been approved for treatment of familial adenomatous polyposis (FAP), and COX-2 inhibitors are currently being studied in other cancer types such as breast cancer.

Non-limiting examples of COX-2 inhibitors include celecoxib, rofecoxib, sulindac, valdecoxib, etorocoxib, lumiracoxib, paracoxib and amlodipine. In one aspect, the COX-2 inhibitor is celecoxib (CXB).

In various aspects, the therapeutically effective amount of CXB includes about 1-500 mg/day, 50-500 mg/day, 50-200 mg/day or 100-200 mg/day CXB. For example, by "about 100-200 mg/day", it is meant that CXB is to be administered within a dosing range of about 100-200 mg/day for adults. For example, an effective amount of CXB includes about 75, about 80, about 90, about 100, about 110, about 120, about 130, about 14, about 150, about 160, about 170, about 180, about 190, about 200, about 210, or about 225 mg/day CXB, for an adult subject (e.g., 18-year-old and older). The dosing range can be adjusted for the treatment of children, following rules and guidelines known in the art.

In one aspect, the administration of MBZ is concurrent with the administration of CXB. For example, in various aspects, the administration of about 25-50 mg/kg MBZ is concurrent with the administration of about 100-200 mg/day CXB.

In another embodiment, the invention provides a method of reducing the risk of developing a NF1-related malignancy or cancer in a subject having NF1 including administering to the subject a therapeutically effective amount of MBZ, thereby reducing the risk of developing a NF1-related malignancy or cancer.

The therapeutically effective amount of MBZ is administered at a dosing schedule sufficient to have a therapeutic effect in the subject. In various aspects, the administration of about 25-50 mg/kg MBZ is based on a daily dosing schedule.

In one aspect, the NF1-related cancer is MPNST.

As described above, the administration of MBZ inhibits or reduces NF1-related cancer cell growth by reducing Ras activation, reducing GTP-bound Ras levels and/or reducing phospho-ERK (pERK) levels.

By reducing Ras activation, GTP-bound Ras levels and/or pERK levels the methods provided herein reduce cancer cell growth and thereby reduce the risk of development of a NF1-related malignancy or cancer. By reducing the risk of development of a NF1-related malignancy or cancer, it is meant that the method is used before the health effects occur or at the earliest stage of the disease. As discussed above, the method described herein provides primary, secondary or tertiary prevention to subjects that are at-risk of developing NF1-related malignancies, and that are therefore closely monitored for such development.

NF1 disease is a hereditary disease that predisposes to the development of NF1-related malignancies or cancer. Therefore, subjects may be diagnosed with the disease yet not have developed any symptoms or NF1-related malignancies or cancer. In other cases, the subject may have been diagnosed with the disease and have developed symptoms of NF1 but no NF1-related malignancies or cancer (yet). Lastly, the subject may have been diagnosed with the disease and have developed symptoms of NF1 and NF1-related malignancies. The methods described herein are especially promising for NF1 patients that have not yet developed any malignancy or cancer.

In other aspects, the method further includes administering to the subject a therapeutically effective amount of a COX-2 inhibitor.

In some aspects, the COX-2 inhibitor is CXB.

In an additional embodiment, the invention provides a pharmaceutical composition including a therapeutically effective amount of MBZ, a therapeutically effective amount of a COX-2 inhibitor and a pharmaceutically acceptable carrier.

As used herein, "pharmaceutical composition" refers to a formulation comprising an active ingredient, and optionally a pharmaceutically acceptable carrier, diluent or excipient. The term "active ingredient" can interchangeably refer to an "effective ingredient" and is meant to refer to any agent that is capable of inducing a sought-after effect upon administration. In one embodiment, the active ingredient includes a biologically active molecule. As used herein, the phrase "biologically active molecule" refers to a molecule that has a biological effect in a cell. In certain embodiments the active molecule may be an inorganic molecule, an organic molecule, a small organic molecule, a drug compound, a peptide, a polypeptide, such as an enzyme or transcription factor, an antibody, an antibody fragment, a peptidomimetic, a lipid, a nucleic acid such as a DNA or RNA molecule, a ribozyme, hairpin RNA, siRNA (small interfering RNAs) of varying chemistries, miRNA, siRNA-protein conjugate, an siRNA-peptide conjugate, and siRNA-antibody conjugate, an antagomir, a PNA (peptide nucleic acid), an LNA (locked nucleic acids), or a morpholino. In certain illustrative embodiments, the active agents include MBZ and a COX-2 inhibitor.

By "pharmaceutically acceptable" it is meant the carrier, diluent or excipient must be compatible with the other ingredients of the formulation and not deleterious to the recipient thereof, nor to the activity of the active ingredient of the formulation. Pharmaceutically acceptable carriers, excipients or stabilizers are well known in the art, for example Remington's Pharmaceutical Sciences, 16th edition, Osol, A. Ed. (1980). Pharmaceutically acceptable carriers, excipients, or stabilizers are nontoxic to recipients at the dosages and concentrations employed, and may include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (for example, Zn-protein complexes); and/or non-ionic surfactants such as TWEEN™, PLURONICS™ or polyethylene glycol (PEG). Examples of carrier include, but are not limited to, liposome, nanoparticles, ointment, micelles, microsphere, microparticle, cream, emulsion, and gel. Examples of excipient include, but are not limited to, anti-adherents such as magnesium stearate, binders such as saccharides and their derivatives (sucrose, lactose, starches, cellulose, sugar alcohols and the like) protein like gelatin and synthetic polymers, lubricants such as talc and silica, and preservatives such as antioxidants, vitamin A, vitamin E, vitamin C, retinyl palmitate, selenium, cysteine, methionine, citric acid, sodium sulfate and parabens. Examples of diluent include, but are not limited to, water, alcohol, saline solution, glycol, mineral oil and dimethyl sulfoxide (DMSO).

For example, the polymorph C form of MBZ is orally administered to adult subjects at a dose of about 25-50 mg/kg daily.

In one aspect, the COX-2 inhibitor is CXB.

For example, in one aspect the polymorph C form of MBZ is orally administered to adult subjects at a dose of about 25-50 mg/kg daily concurrently with CXB at a dose of about 100-200 mg/day orally.

In a further embodiment, the invention provides a method of reducing the risk of developing a NF1-related malignancy or cancer in a subject having NF1 including administering to the subject a composition including a therapeutically effective amount of MBZ, a therapeutically effective amount of a COX-2 inhibitor and a pharmaceutically acceptable carrier, thereby reducing the risk of developing a NF1-related malignancy or cancer.

In yet another embodiment, the invention provides a method of preventing or delaying the development of a NF1-related malignancy or cancer in a subject having NF1 including administering to the subject a composition including a therapeutically effective amount of MBZ, a therapeutically effective amount of a COX-2 inhibitor and a pharmaceutically acceptable carrier, thereby preventing the development of the NF1-related malignancy.

In various aspects, the NF1-related malignancy or cancer is selected from the group consisting of malignant peripheral nerve sheath tumor (MPNST), astrocytoma, breast cancer, rhabdomyosarcoma, pheochromocytoma, gastrointestinal stromal tumor (GIST), malignant fibrous histiocytoma and thyroid cancer.

In one embodiment, the invention provides a kit for reducing the risk of developing, preventing the development of or delaying the development of a NF1-related malignancy or cancer including a pharmaceutical composition of MBZ and instructions for using MBZ.

In one aspect, the pharmaceutical composition further includes a COX-2 inhibitor.

In another embodiment, the invention provides a method of treating a NF1-related malignancy or cancer in a subject having NF1 including administering to the subject a therapeutically effective amount of MBZ, thereby treating the NF1-related malignancy or cancer. In some aspects, the method further includes administering to the subject a therapeutically effective amount of a COX-2 inhibitor.

In yet another embodiment, the invention provides a method of treating a NF1-related malignancy or cancer in a subject having NF1 including administering to the subject a composition including a therapeutically effective amount of MBZ, a therapeutically effective amount of a COX-2 inhibitor and a pharmaceutically acceptable carrier, thereby treating the NF1-related malignancy or cancer.

The term "treatment" is used interchangeably herein with the term "therapeutic method" and refers to both 1) therapeutic treatments or measures that cure, slow down, lessen symptoms of, and/or halt progression of a diagnosed pathologic conditions or disorder, and 2) and prophylactic/preventative measures. Those in need of treatment may include individuals already having a particular medical disorder as well as those who may ultimately acquire the disorder (i.e., those needing preventive measures).

Presented below are examples discussing the use of mebendazole alone or in combination with a cyclooxygenase-2 inhibitor contemplated for the discussed applications. The following examples are provided to further illustrate the embodiments of the present invention but are not intended to limit the scope of the invention. While they are typical of those that might be used, other procedures, methodologies, or techniques known to those skilled in the art may alternatively be used.

EXAMPLES

Example 1

Material and Methods

Tissue Culture and Cell Lines

The human NF1-associated MPNST cell line NF90.8 was privately provided and sNF96.2 was purchased from the American Type Culture Collection. Cells were cultured in DMEM supplemented with 10% fetal bovine serum (FBS) and penicillin/streptomycin. These cell lines were not authenticated. All cells were tested and found free of *mycoplasma* contamination.

Reagents and Antibodies

Rabbit anti-Nf1 antibody was purchased from Bethyl Laboratories and anti-βActin horseradish peroxidase (HRP) antibody was purchased from Santa Cruz Biotech. An Active Ras Detection Kit, including the anti-Ras antibody, was purchased from Cell Signaling Technology.

Assays

A Ras activity assay was performed according to the manufacturer's instructions for the Active Ras Detection Kit. Briefly, cells were lysed with the Lysis/Binding/Wash buffer and pelleted, then the supernatant was used as the cell lysate. In the positive control, 5 µL of 10 mM GTPγS was added to 500 µL of lysates and incubated at 30° C. for 15 min. Cell lysates were incubated with glutathione resin, together with the purified GST-Raf1-RBD protein at 4° C. for 1 h in a spin cup. The resin was washed, and the bound proteins were eluted by incubating with dithiothreitol (DTT)-containing sample buffer at RT for 2 min. Eluted samples were heated and analyzed by anti-Ras Western blotting.

A cell proliferation assay was performed using Cell Counting Kit-8. Cells in 100 µL media in a 96-well plate were incubated with 10 µL of WST-8, a tetrazolium salt, at 37° C. in a tissue culture incubator. Absorbance was measured at 450 nm. Half maximal inhibitory concentrations (IC50s) were determined by incubating cells at a range of concentrations for 72 h and were calculated using the log (inhibitor) vs. response function and non-linear fit.

Chemoprevention in NPcis Mice

NPcis (cis Nf1+/−; Tp53+/−) mice in C57BL/6 background (B6;129S2-Trp53tm1Tyj Nf1tm1Tyj/J) were bred by pairing male heterozygous NPcis mice with the female wildtype mice to better generate MPNST animals. Since homozygous Nf1/Tp53 KO mice are embryonically lethal, only heterozygous and wildtype pups were born. Like NF1 patients, NPcis mice spontaneously develop predominantly soft tissue sarcomas including MPNSTs (genetically engineered murine (GEM) PNSTs) and malignant Triton tumors, as well as rhabdomyosarcomas and astrocytomas that severely limit their life expectancy to ~5 months. The addition of heterozygous Tp53 knock-out (KO) accelerates the cancer development, which mimics the secondary mutations required for the transformation to malignancies such as MPNST, where the second copy of Nf1 is also lost due to the loss of heterozygosity (LOH).

Mice were genotyped via qPCR using the following primer pairs:

| Nf1 wildtype (WT) | 5'-GGTATTGAATTGAA GCACCTTTGTTTGG-3' | SEQ ID NO: 1, |
|---|---|---|
| | 5'-CGTTTGGCATCATC ATTATGCTTACA-3' | SEQ ID NO: 2, |
| reporter: Nf1 KO | 5'-AATATATGACCCCA TGGCTGTC-3' | SEQ ID NO: 3, |
| | 5'-TGGAGAGGCTTTTT GCTTCCT-3' | SEQ ID NO: 4, |
| | 5'-CGTTTGGCATCATC ATTATGCTTACA-3' | SEQ ID NO: 5, |
| reporter: Tp53 WT | 5'-CTGCTCGACATGGC TG-3' | SEQ ID NO: 6, |
| | 5'-GTGAGGTAGGGAGC GACTTC-3' | SEQ ID NO: 7, |
| | 5'-TTGTAGTGGATGGT GGTATACTCAGA-3' | SEQ ID NO: 8, |
| Reporter: Tp53 KO | 5'-CCTGGATCCTGTGT CTTC-3' | SEQ ID NO: 9, |
| | 5'-TGTTTTGCCAAGTT CTAATTCCATCAGA-3' | SEQ ID NO: 10, |
| | 5'-TTGTAGTGGATGGT GGTATACTCAGA-3' | SEQ ID NO: 11, |
| reporter: | 5'-ACAGGATCCTCTAG AGTCAG-3' | SEQ ID NO: 12 |

At day 60 after birth, heterozygous mice were started on the medicated feed or water. The mouse diet consisting of 45 kcal % fat containing soybean oil and lard for fat was used as the control feed. Diets with 175, 195, 215 or 250 mg/kg of MBZ polymorph C or 1000 ppm (mg/kg) celecoxib were manufactured. Sulindac was added to drinking water at 160 ppm (0.5 mg/day) in 4 mM sodium phosphate buffer as previously described. Animals were palpated weekly for tumors and survival and cause of death were recorded.

Immunohistochemistry

Mouse tumors were first fixed by formalin and embedded in paraffin. For hematoxylin & eosin (H&E) staining, the section was de-paraffinized and stained by the standard hematoxylin and eosin procedure to visualize tissue structures. For immunostaining, rabbit anti-Erk1/2 and anti-pErk1/2 antibodies were used. Sections were de-paraffinized using a standard procedure and blocked using 1.9% $H_2O_2$ in methanol at room temperature for 10 min. Sections were heated at 100° C. for 20 min in the antigen retrieval citrate solution and blocked by the serum-free protein blocker for 5 min at room temperature. After incubation with the rabbit anti-Erk1/2 or anti-pErk1/2 antibody diluted at 1:50 overnight at 4° C., biotin-conjugated anti-rabbit IgG was applied for 20 min at room temperature, followed by washing and incubation with streptavidin peroxidase for 15 min at room temperature. Antibody binding was visualized by the 3,3'-Diaminobenzidine (DAB) chromogen system. Subsequently, sections were counterstained by hematoxylin. Immunohistochemistry (IHC) quantification of representative tumor tissue sections was carried out with open source software using JPEG files. Mean optical density (OD) was calculated as the log average (maximal intensity/mean intensity) after image processing with color deconvolution and background subtraction.

Statistical Analysis

The results are presented as a mean value plus or minus the standard deviation. The p-values were determined by a Mantel-Cox test. A p-value under 0.05 was accepted as statistically significant.

Figure 1B:
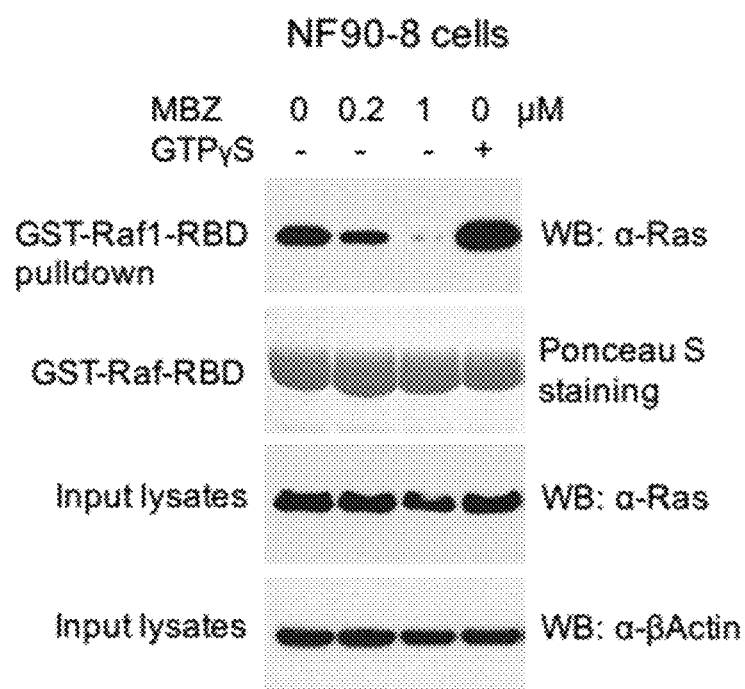

Example 2 Mebendazole Inhibited NF1-Derived MPNST Cell Lines Through Ras Inhibition Human MPNST cells NF90-8 and sNF96.2, both derived from NF1 patients, were treated with various MBZ concentrations for 72 h. As illustrated in FIG. 1A, the results revealed favorable IC50 levels at 0.18 and 0.32 µM, respectively. Because NF1-associated tumors are mainly driven by Ras hyperactivation, MBZ's ability to inhibit Ras activity in the NF90-8 cell line was studied by exposing NF90-8 cells to different concentrations of MBZ (0.2 and 1 µM) for 24 h. The activated form of GTP-bound Ras, detected by GST-Raf1-RBD fusion protein binding, was reduced in MBZ-treated NF90-8 cells in a concentration-dependent manner (FIG. 1B). This confirmed the Ras inhibitory effect of MBZ in vitro.

Example 3 Mebendazole Delayed Tumor Formation and Improves Survival In NPcis MICE Cis Nf1+/−; Tp53+/−(NPcis) mice are naturally predisposed to a number of solid malignancies, which typically form ~3-5 months after birth. 77% will develop soft tissue sarcomas—of which 60-65% are MPNSTs, 20% malignant Triton tumors, 10% rhabdomyosarcomas, 10% leiomyosarcomas and fibrohistiocytomas, 14% lymphomas, 8% carcinomas, and 1% neuroblastomas; astrocytomas have also been reported.

Figure 2A:
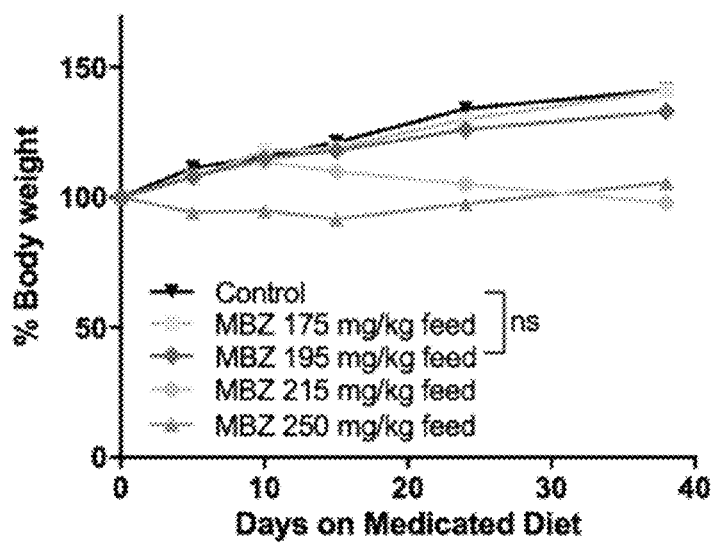
FIGS. 2A-2B illustrate the dose-dependent toxicity of MBZ in cis NF1+/−; Tp53+/−(NPcis) mice.
Figure 2B:
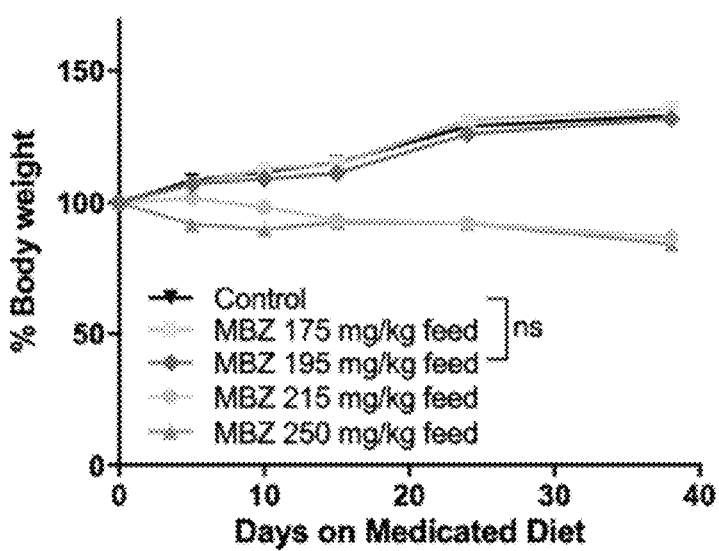

To determine the most effective and tolerable long-term MBZ dose in vivo, 60-day old male and female NPcis mice were separated into groups and provided with control feed or continuous medicated feed containing 175, 195, 215 or 250 mg/kg MBZ. This range was calculated based on previously established maximal dose of 50 mg/kg MBZ via oral gavage and the estimated daily food intake of a mouse. Mice were weighed weekly and examined for signs of toxicity over 4 weeks. In the higher MBZ dosing groups of 250 and 215 mg/kg diets, nearly all mice showed evidence of excessive toxicity, including ruffled fur and significant weight loss between 10-15% thereby precluding the long-term use of those doses and establishing 195 mg/kg MBZ feed as the most suitable diet for long-term chemoprevention in these mice (FIGS. 2A and 2B).

In order to investigate the tumor-preventative effects of MBZ, continuous oral administration of MBZ via 195 mg/kg feed was initiated at 60 days after birth, before the formation of any malignancies. Mice were palpated weekly for the presence of any tumors. For the purpose of this study, 'Solid Malignancies' were defined as any type of sarcoma and astrocytoma, in addition to neuroblastomas and carcinomas, while 'Others' included non-solid malignancies such as lymphomas, leukemias and unknown causes of death.

Figure 3A:
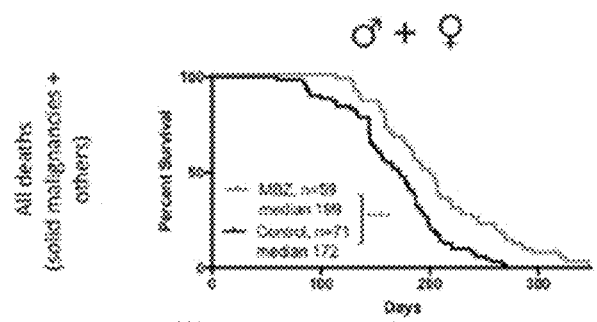
FIGS. 3A-3L illustrate the effect of MBZ on the onset of cancer and survival in NPcis mice.
Figure 3B:
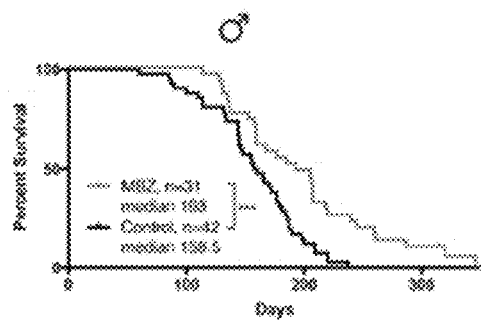
Figure 3C:
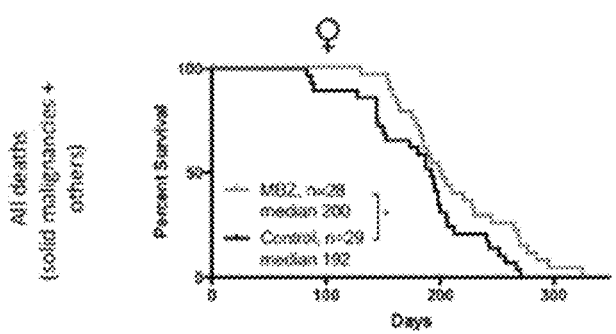
Figure 3D:
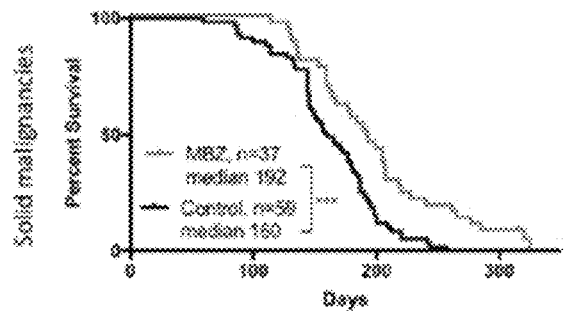
Figure 3E:
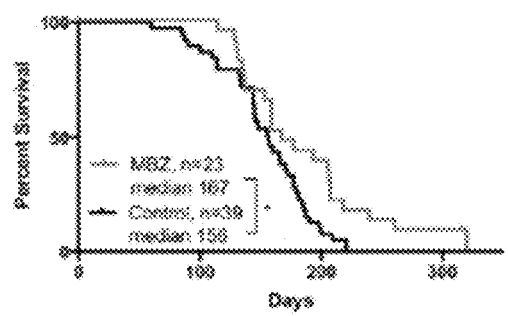
Figure 3F:
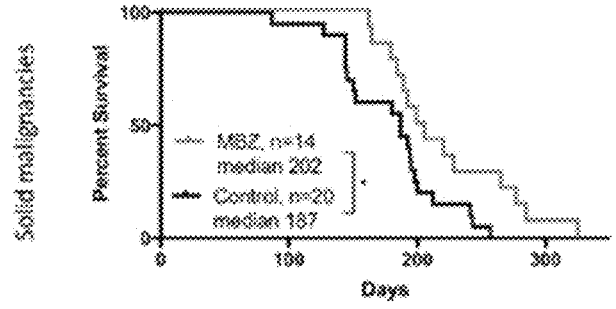
Figure 3G:
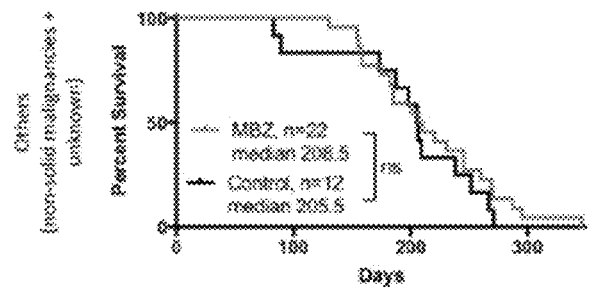
Figure 3H:
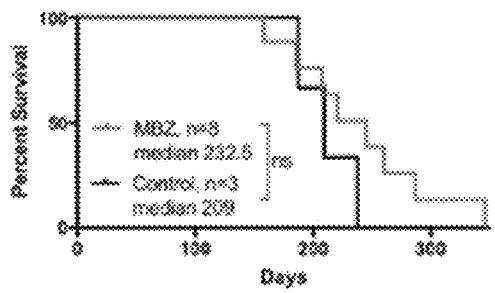
Figure 3I:
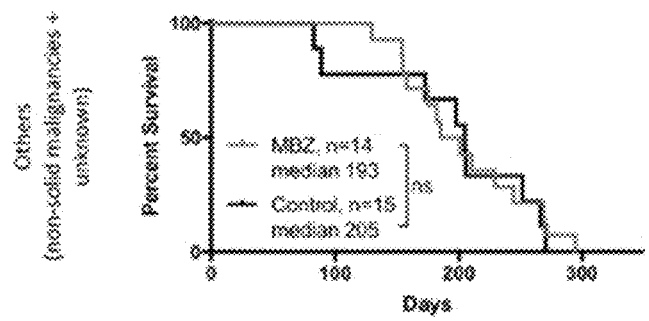
Figure 3J:
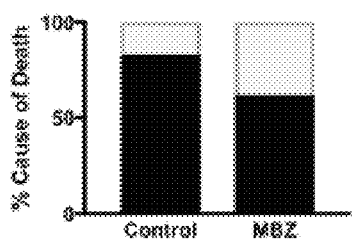
Figure 3K:
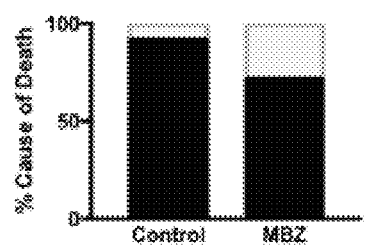
Figure 3L:
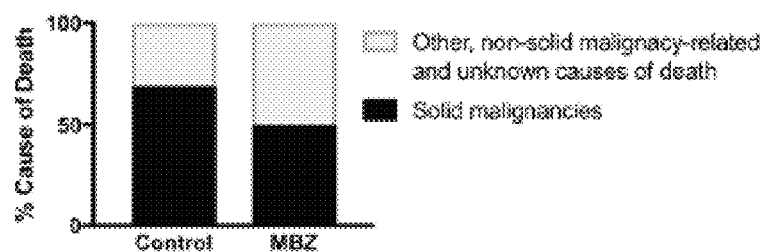

MBZ treatment started at the age of 60 days significantly increased the overall median survival for male, female and combined cohorts (FIGS. 3A, 3B and 3C). In MBZ-treated mice, the time to tumor occurrence was significantly delayed compared to untreated control animals: 50% of all control mice had developed tumors and succumbed to disease by the age of 160 days, whereas in the MBZ-treated cohort, the tumor occurrence and median mortality was delayed by 32 days to 192 days (FIGS. 3D, 3E and 3F). Although observed in male and female NPcis mice alike, MBZ's cancer preventative effect appeared to be more pronounced in males, with an increase in median survival by 34.5 days compared to 14 days in female mice (FIGS. 3D, 3E and 3F). FIGS. 3G, 3H and 3I demonstrated that MBZ's chemopreventative effect was specific to mice with solid malignancies and did not affect the median survival of other, i.e., non-solid malignancy-related and unknown, causes of death both in male and female mice (FIGS. 3G, 3H and 3I). Lastly, MBZ treatment resulted in a ~25% reduction in solid cancer-related causes of death, thus demonstrating the feasibility of such a cancer prevention strategy in these NPcis mice (FIGS. 3J, 3K and 3L).

Example 4 Mebendazole Reduced Perk Activity in Tumors In Vivo

Figure 4:
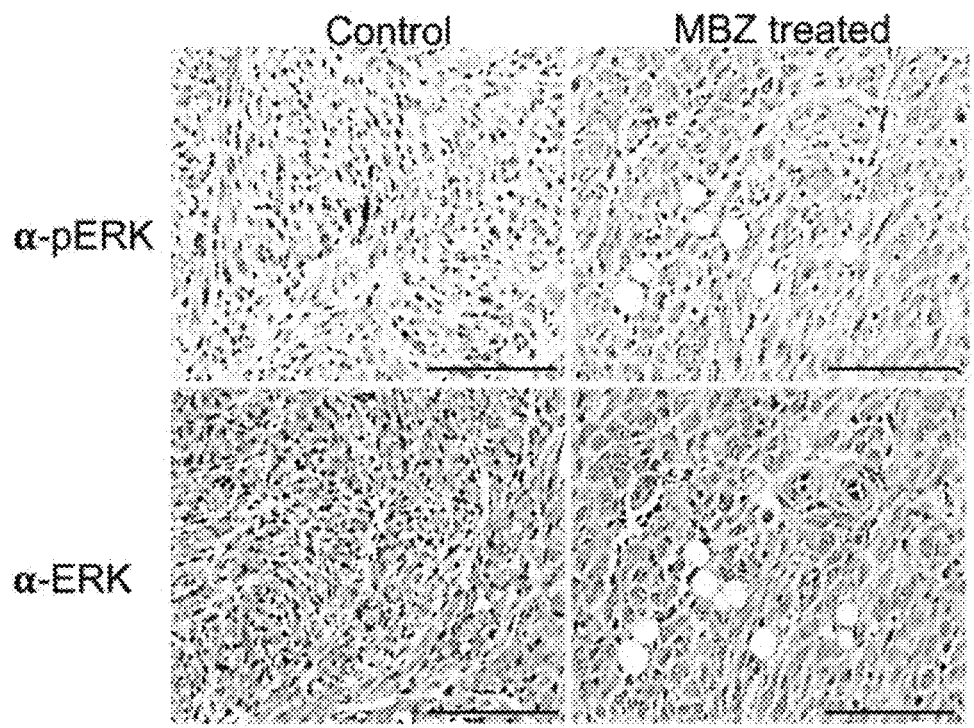
FIG. 4 shows representative images of immunochemically strained tumors from untreated (left) and MBZ-treated (right) NPcis mice, stained for pERK1/2 (upper row) and ERK1/2 (lower row).

In NPcis mice, the loss of Nf1 leads to the hyperactivation of Ras, with the subsequent activation of the downstream effector ERK that is reflected by elevated levels of phosphorylated ERK (pERK) in MPNSTs and other related tumors. Immunohistochemistry showed that continuous MBZ treatment with a 195 mg/kg diet reduced pERK levels in sarcomas of NPcis mice compared to untreated mice (FIG. 4). An analysis of the DAB staining intensity in three independent MBZ-treated tumor samples confirmed these results, with a reduced mean optical density (OD) of 0.02 in MBZ-treated samples compared to 0.05 in controls, while ERK staining was similar between both groups, with mean intensities of 0.07 and 0.08 for MBZ-treated and untreated tumors, respectively (FIG. 4).

Figure 5A:
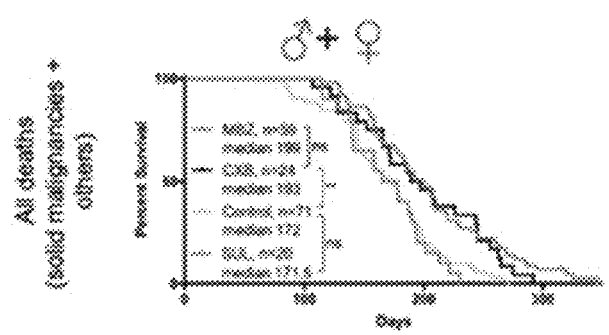
FIGS. 5A-5L illustrate the effect of MBZ and cyclooxygenase-2 inhibitors (celecoxib, CXB and sulindac, SUL) on the onset of cancer and survival in NPcis mice.
Figure 5B:
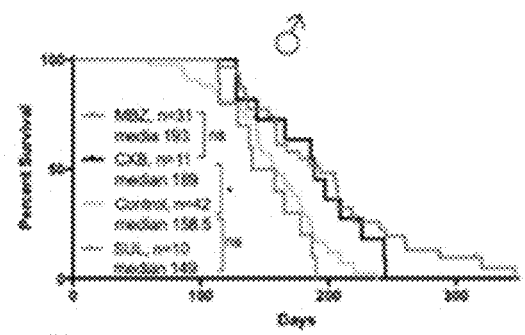
Figure 5C:
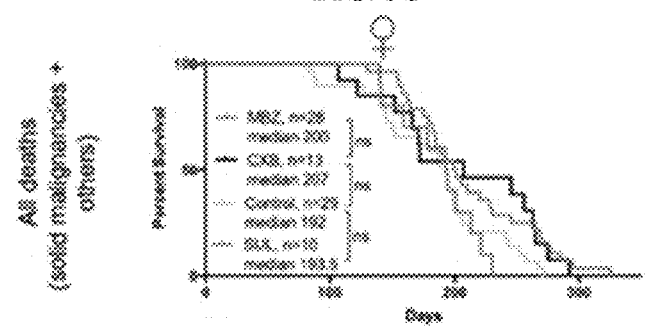
Figure 5D:
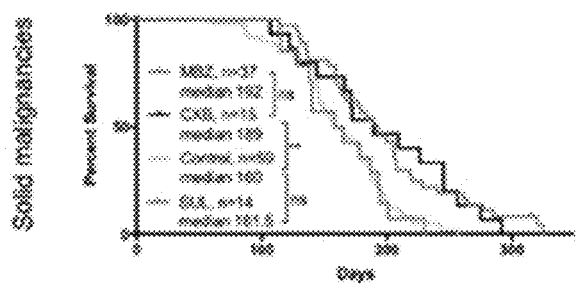
Figure 5E:
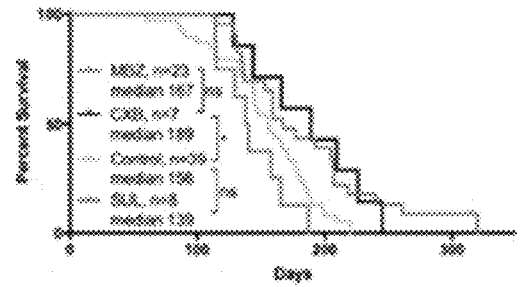
Figure 5F:
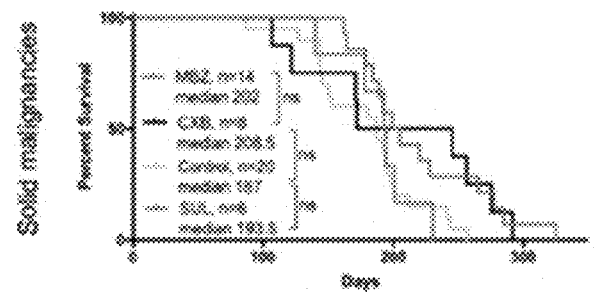
Figure 5G:
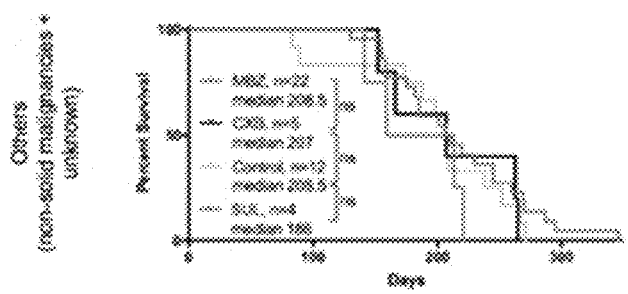
Figure 5H:
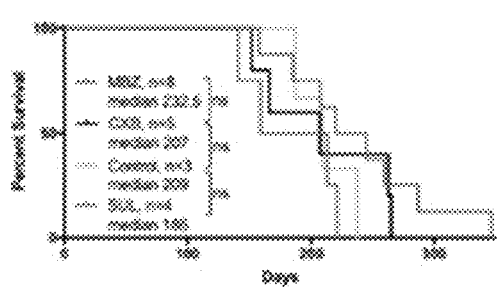
Figure 5I:
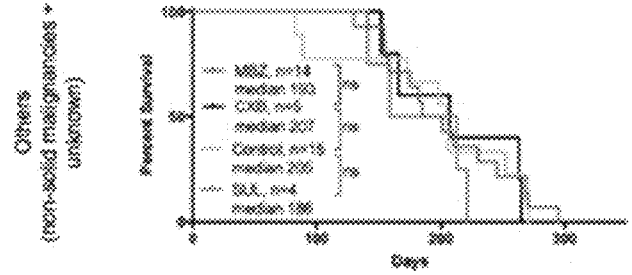
Figure 5J:
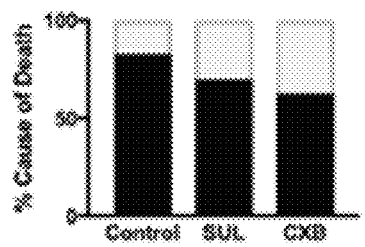
Figure 5K:
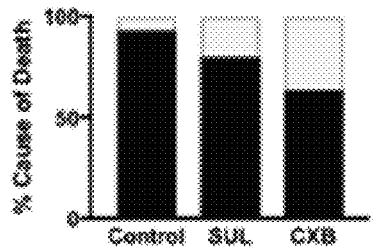
Figure 5L:
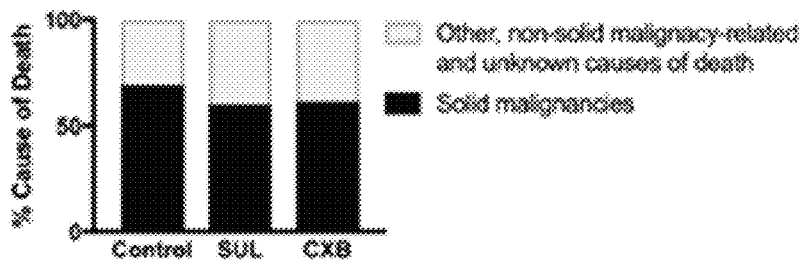

Example 5 Cancer-Preventative Effects of Celecoxib and Mebendazole are Similar in NPcis Mice The antitumor effect of selective COX-2 inhibitors, such as sulindac (SUL) and celecoxib (CXB), has been shown in several malignancies and cancer predisposition syndromes. In the NPcis mouse model, it was found that MBZ-treated mice had a longer overall median survival of 199 days compared to CXB, with 193 days; however, this difference was not statistically significant (FIGS. 5A, 5B and 5C). When compared to untreated controls, CXB's effect on median survival was statistically increased in male NPcis mice with solid malignancies, while female mice showed a notable, but statistically insignificant, increase in survival compared to controls. Furthermore, CXB was substantially more effective in delaying the onset of malignancies than SUL, which showed a median survival of 171.5 days and failed to demonstrate any effect in male or female mice compared to controls (FIGS. 5A-5F). Like MBZ, neither SUL nor CXB had an effect on the survival of non-cancer related causes (FIGS. 5G, 5I and 5I). Consistent with these findings, a ~25% decline in cancer-related cause of death in CXB-treated mice was also noticed (FIGS. 5J, 5K and 5L).

Example 6 Mebendazole is More Effective than Combined MBZ with CXB

Figure 6A:
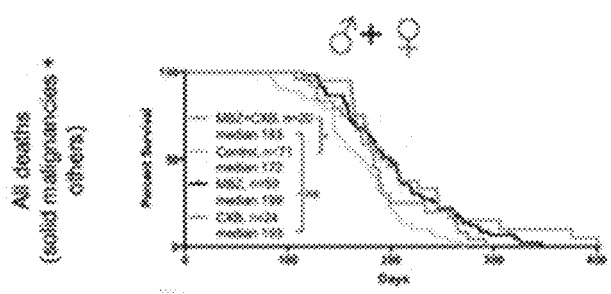
FIGS. 6A-6L illustrate the effect of MBZ in combination with CXB on the onset of cancer and survival in NPcis mice.
Figure 6B:
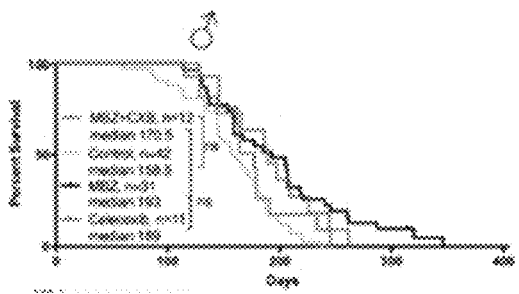
Figure 6C:
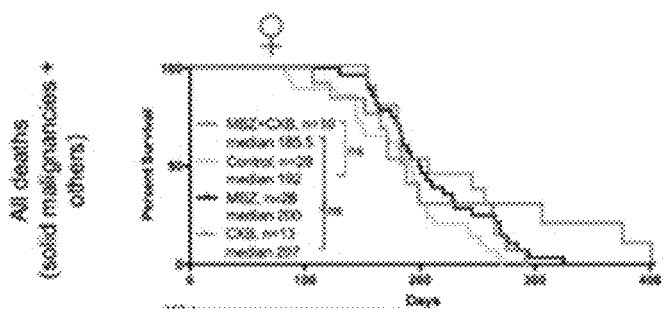
Figure 6D:
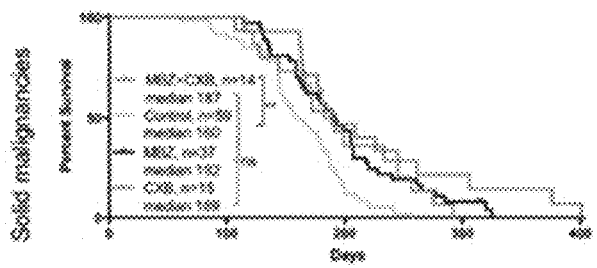
Figure 6E:
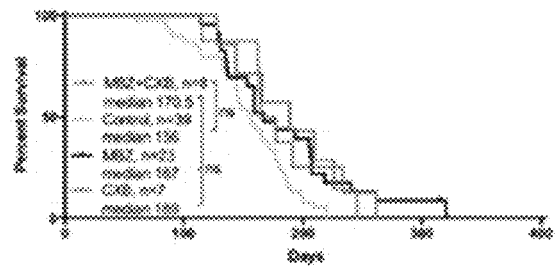
Figure 6F:
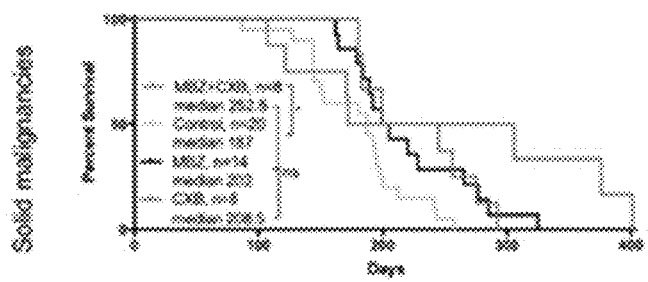
Figure 6G:
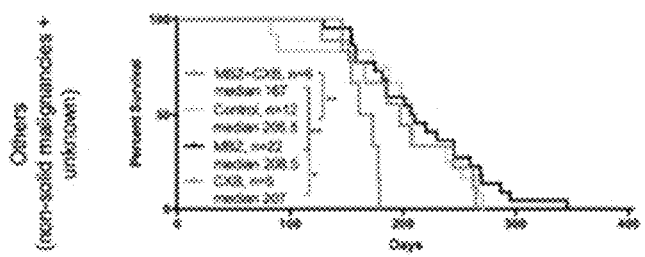
Figure 6H:
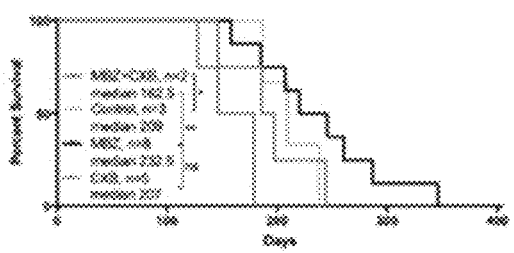
Figure 6I:
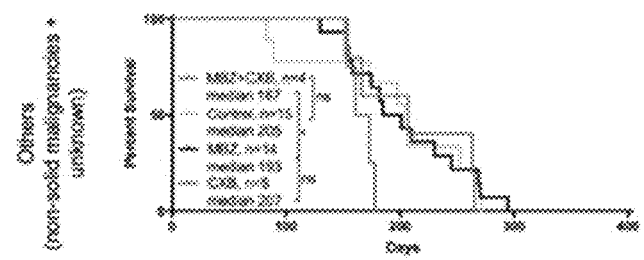
Figure 6J:
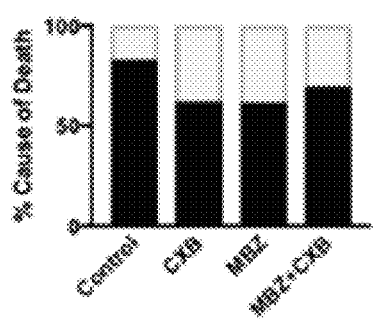
Figure 6K:
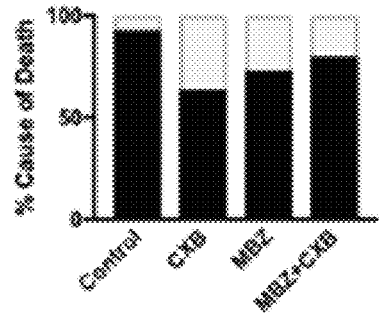
Figure 6L:
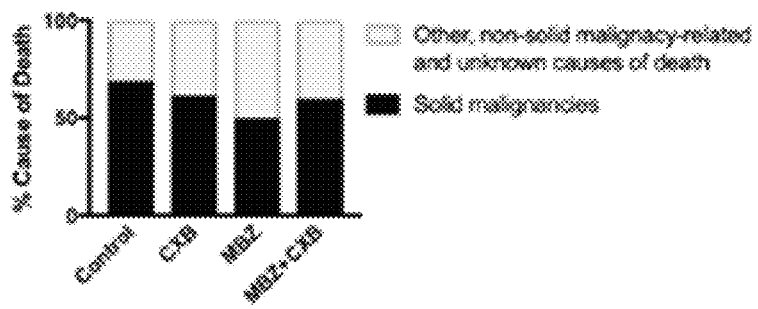

Combined treatment with MBZ and CXB significantly increased median survival in NPcis mice compared to controls. However, the observed overall survival benefit appeared inferior to the effect achieved by MBZ or CXB alone, however, the difference is not statistically significant (FIGS. 6A, 6B and 6C). When investigating gender-specific effects, it was found that dual use of MBZ and CXB in female NPcis mice was successful in delaying solid cancer occurrence and substantially enhancing the median survival beyond what was achieved by each agent alone and untreated controls (FIGS. 6D, 6E and 6F). This stands in contrast to male mice with solid malignancies, who did not experience any additional survival benefits from the combination treatment in comparison to single agent MBZ or CXB (FIGS. 6D, 6E and 6F). FIGS. 6G, 6H and 6I demonstrated that the combination therapy of MBZ and CXB resulted in an earlier mortality from non-solid cancer-related causes, particularly for male mice, indicating possibly the presence of toxicity, which we had assessed beforehand for each agent separately but not in combination (FIGS. 6G, 6H and 6I). However, the number of mice who died in the MBZ/CXB cohort due to other, non-solid malignancy-related and unknown causes, were small and thus, limiting our ability to conclusively interpret these results. When analyzing cause of death in MBZ/CXB-treated mice, we observed a reduction in solid cancer-related causes in comparison to the controls, as expected, which was largely comparable with what was seen with single agent use (FIGS. 6J, 6K and 6L).

Example 7

DISCUSSION

MBZ's anti-tumor effect in glioblastomas and medulloblastomas is caused by multiple different mechanisms, such as the inhibition of microtubule formation and VEGFR2 autophosphorylation, which was corroborated in various preclinical cancer models and ultimately translated into clinical trials for adult and pediatric patients with cancer. In the current study, MBZ's scope of application was expanded to chemoprevention, i.e., the use of drugs to reduce the risk of cancer development, in high-risk patients of NF1. NF1 is the most common tumor predisposition syndrome in which the loss of tumor suppressor neurofibromin leads to the activation of the Ras proto-oncogene and the development of dozens of benign and malignant tumors. MPNSTs and gliomas are the most common NF1-specific cancers, accounting for 63% of malignancies and a substantial mortality burden in adults younger than 40 years of age; other sarcomas (e.g., rhabdomyosarcomas), gastrointestinal stromal tumors, pheochromocytomas and breast cancers may also occur at a higher frequency compared to the non-affected population. MPNSTs in NF1 patients have been particularly recalcitrant to treatment, with overall survival times that are shorter than those of patients with spontaneous MPNSTs. Surgical removal of a high-risk, pre-cancerous lesion is the only prophylactic modality that may reduce mortality but has unfortunately been associated with morbidity.

In this study, it was found that MBZ inhibited the growth of NF1-related MPNST cells in vitro and substantially delayed tumor formation in NPcis mice when initiated 60 days after birth, without overt disease. Interestingly, the effect was different between genders, with male mice experiencing a more substantial protective effect than female mice, who tend to develop tumors later than their male counterparts and have a longer median survival. A similar observation was made in mice treated with combined CXB with MBZ, which resulted in the largest delay in tumor occurrence and superior median survival in female mice, while males did not experience any benefit from the combination therapy compared to single agent MBZ or CXB. Notably, the male bias of NPcis mice in developing MPNST has been reported before. Intrinsic factors such as the tumor microenvironment, inflammation and differences in the sex hormones may be potential causes of this phenomenon; however, the underlying mechanism is unclear and should be investigated further in animals and humans. MBZ's cytotoxic effect on NF1-related malignancies may result from a reduction in activated GTP-bound Ras and a subsequent decrease in pERK in MBZ-treated malignancies in vivo, thus directly targeting the molecular underpinnings for tumor development in this condition. The potential significant impact of such chemoprevention on the mortality rate of cancer in the NF1 patient population can be envisioned from the success of NSAIDs and other agents on reducing the risk of colorectal, prostate and breast cancer. By demonstrating the feasibility of a chemopreventative approach for NF1, this study stimulates a rational approach to interrogate already existing databases for drugs that appear to decrease Ras activity and/or increase NF1 expression as a preventative drug discovery pipeline in these patients in order to reduce cancer occurrence and mortality.

Chemoprevention may involve the perturbation of a variety of steps in tumor initiation, promotion and progression. As such, COX-2 overexpression leads to cancer cell proliferation, neovascularization, and suppression of apoptosis and thus is associated with a worse prognosis in various malignancies, especially sarcomas. It is therefore not surprising that overexpression of COX-2 has also been observed in NF1-associated MPNSTs and that selective COX-2 inhibition had an antitumor effect on these cells. This study confirmed these results and showed that the selective COX-2 inhibitor CXB, but not the non-selective COX inhibitor SUL, delayed cancer occurrence and increased median survival in both male and female NPcis mice.

Effective chemoprevention requires the need to identify a high-risk patient population and compounds or drug combinations with very low toxicity to allow long-term use in humans. When initiated 60 days after birth, long-term daily continuous MBZ administration was well tolerated in male and female NPcis mice, with stable weights using 195 mg/kg MBZ feed. This is in line with human data, which demonstrate a >40-year history of safe and continuous use for parasitic infections and cystic echinococcosis. This, along with the observed Ras inhibitory effect, could make MBZ an attractive candidate for long-term chemoprevention in the NF1 patient population. It should be noted that rigorous monitoring for adverse reactions would be required, as unexpected and expected toxicities could develop from long-term use of cancer preventative agents, particularly when multiple agents are used, and the benefits should clearly outweigh any potential risks. Given the heterogeneity of clinical symptoms among NF1 patients, it is doubtful that all NF1 patients would experience the same benefits and patient groups at high or low risk would have to be defined. For example, the low-risk NF1 population would include individuals with NF1 Arg1809, NF1 Arg1038Gly, NF1 Met992del, and NF1 Met1149 mutations, all of which are known not to develop any tumors or malignancies. In contrast, the largest benefit would likely be observed in patients with a severe phenotype characterized by a higher tumor burden and a higher risk of malignancies. This group of patients would include individuals with large Nf1 microdeletions, in which the lifetime risk for MPNST is increased to 16-26%; patients with an NF1 p. 844-848 missense mutation, who have a higher predisposition for symptomatic neurofibromas, optic pathway gliomas and malignancies compared with the general NF1-affected population and NF1 patients with Arg1276 variants, who are also at a higher risk of developing symptomatic tumors and MPNSTs.

In summary, this data lays an important foundation for the effective and feasible chemoprevention of malignancies in patients with NF1, which has the potential to delay or prevent the malignant transformation of MPNST and other NF1-related malignancies, decrease the need for surgical intervention and reduce the use of antineoplastic therapies in this patient population.

Although the invention has been described with reference to the above examples, it will be understood that modifications and variations are encompassed within the spirit and scope of the invention. Accordingly, the invention is limited only by the following claims.

What is claimed is:

1. A method of delaying the development of a neurofibromatosis type 1 (NF1)-related malignancy or cancer in a subject having NF1 comprising administering to the subject a therapeutically effective amount of mebendazole (MBZ), thereby delaying the development of the NF1-related malignancy or cancer.

2. The method of claim 1, wherein the NF1-related malignancy or cancer is selected from the group consisting of malignant peripheral nerve sheath tumor (MPNST), astrocytoma, breast cancer, rhabdomyosarcoma, pheochromocytoma, gastrointestinal stromal tumor (GIST), malignant fibrous histiocytoma and thyroid cancer.

3. The method of claim 2, wherein the NF1-related cancer is MPNST.

4. The method of claim 1, wherein MBZ inhibits or reduces NF1-related cancer cell growth.

5. The method of claim 4, wherein inhibiting or reducing NF1-related cancer cell growth comprises reducing Ras activation, reducing GTP-bound Ras levels and/or reducing phospho-ERK (PERK) levels in NF1-related cancer cells.

6. The method of claim 1, wherein administering MBZ increases survival of the subject.

7. The method of claim 1, wherein the therapeutically effective amount of MBZ comprises from about 25 to 50 mg/kg MBZ.

8. The method of claim 1, further comprising administering to the subject a therapeutically effective amount of a cyclooxygenase-2 (COX-2) inhibitor.

9. The method of claim 8, wherein the COX-2 inhibitor is celecoxib (CXB).

10. The method of claim 9, wherein therapeutically effective amount of CXB comprises from about 100 to 200 mg/day CXB.

11. A method of reducing the risk of developing a neurofibromatosis type 1 (NF1)-related malignancy or cancer in a subject having NF1 comprising administering to the subject a therapeutically effective amount of mebendazole (MBZ), thereby reducing the risk of developing an NF1-related malignancy or cancer.

12. The method of claim 11, wherein the NF1-related cancer is MPNST.

13. The method of claim 11, wherein MBZ inhibits or reduces NF1-related cancer cell growth.

14. The method of claim 13, wherein the inhibiting or reducing NF1-related cancer cell growth comprises reducing Ras activation, reducing GTP-bound Ras levels and/or reducing phospho-ERK (PERK) levels in NF1-related tumor cells.

15. The method of claim 11, further comprising administering to the subject a therapeutically effective amount of a cyclooxygenase-2 (COX-2) inhibitor.

16. The method of claim 15, wherein the COX-2 inhibitor is celecoxib (CXB).

17. A method of reducing a risk of developing a neurofibromatosis type 1 (NF1)-related malignancy or cancer in a subject having NF1 comprising administering to the subject a pharmaceutical composition comprising a therapeutically effective amount of mebendazole (MBZ) and a therapeutically effective amount of a cyclooxygenase-2 (COX-2) inhibitor, thereby reducing the risk of developing an NF1-related malignancy or cancer.

18. A method of delaying the development of a neurofibromatosis type 1 (NF1)-related malignancy or cancer in a subject having NF1 comprising administering to the subject a pharmaceutical composition comprising a therapeutically effective amount of mebendazole (MBZ) and a therapeutically effective amount of a cyclooxygenase-2 (COX-2) inhibitor, thereby delaying the development of NF1-related malignancy or cancer.

19. A method of improving survival of a subject having a neurofibromatosis type 1 (NF1)-related malignancy or cancer comprising administering to the subject a therapeutically effective amount of mebendazole (MBZ), thereby improving the survival of the subject.

20. The method of claim 19, further comprising administering to the subject a therapeutically effective amount of a cyclooxygenase-2 (COX-2) inhibitor.

* * * * *

SEQUENCE LISTING

<160> NUMBER OF SEQ ID NOS: 12

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ggtattgaat tgaagcacct ttgtttgg                                            28

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cgtttggcat catcattatg cttaca                                              26

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aatatatgac cccatggctg tc                                                  22

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tggagaggct ttttgcttcc t                                                   21

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cgtttggcat catcattatg cttaca                                              26

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ctgctcgaca tggctg                                                         16

```
<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gtgaggtagg gagcgacttc                                                 20

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ttgtagtgga tggtggtata ctcaga                                          26

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cctggatcct gtgtcttc                                                   18

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tgttttgcca agttctaatt ccatcaga                                        28

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ttgtagtgga tggtggtata ctcaga                                          26

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
acaggatcct ctagagtcag                                                 20
```